United States Patent
Xu

(10) Patent No.: US 8,183,864 B2
(45) Date of Patent: May 22, 2012

(54) SYSTEM FOR MULTI NUCLEUS CARDIAC MR IMAGING AND SPECTROSCOPY

(75) Inventor: Jian Xu, New Hyde Park, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 314 days.

(21) Appl. No.: 12/750,875

(22) Filed: Mar. 31, 2010

(65) Prior Publication Data

US 2010/0264922 A1    Oct. 21, 2010

Related U.S. Application Data

(60) Provisional application No. 61/169,536, filed on Apr. 15, 2009.

(51) Int. Cl.
*G01V 3/00* (2006.01)
(52) U.S. Cl. .......................... 324/307; 324/309
(58) Field of Classification Search .......... 324/300–322; 600/407–445
See application file for complete search history.

(56) References Cited

U.S. PATENT DOCUMENTS

| | | | | |
|---|---|---|---|---|
| 5,792,056 | A * | 8/1998 | Prince | 600/420 |
| 5,865,746 | A | 2/1999 | Murugesan | |
| 7,941,204 | B1 * | 5/2011 | Wang et al. | 600/420 |
| 2008/0116889 | A1 | 5/2008 | Hu et al. | |

OTHER PUBLICATIONS

Szimtenings, M., MRI Hot Topics, Siemens Medical Solutions, Germany.
Applications Guide, Free-breathing 2D-PACE, EPI-DIFF, HASTE TRUFI, TFL and TSE Sequences for Lung and Abdomen, Magnetom Avanto, No. 4 VB11D, syngo MR 2004 V.

* cited by examiner

*Primary Examiner* — Brij Shrivastav
(74) *Attorney, Agent, or Firm* — Alexander J Burke

(57) ABSTRACT

A system for respiratory motion compensated MR imaging or spectroscopy, comprises an MR imaging system. The MR imaging system performs a single imaging scan including, acquiring a first imaging data set representing a spatially localized first imaging region located on a patient diaphragm, using a first RF excitation pulse sequence and by transmitting a nuclei excitation first resonant frequency and receiving data substantially at the first resonant frequency. The MR imaging system derives data representing diaphragm position over a respiratory cycle using the first imaging data set, in the single imaging scan. The MR imaging system in response to determining the diaphragm position is within a predetermined window, acquires a second anatomical imaging data set representing a spatially localized second imaging region using a second RF excitation pulse sequence and by transmitting a nuclei excitation second resonant frequency different to the first resonant frequency and receiving data substantially at the second resonant frequency in the single imaging scan.

13 Claims, 7 Drawing Sheets

SYSTEM FOR MULTI NUCLEUS CARDIAC MR IMAGING AND SPECTROSCOPY

This is a non-provisional application of provisional application Ser. No. 61/169,536 filed 15 Apr. 2009, by Jian Xu.

FIELD OF THE INVENTION

This invention concerns an MR imaging system for respiratory motion compensated MR imaging or spectroscopy, using first and second different RF frequencies to acquire in a single scan, imaging data sets representing a first region used for tracking respiratory movement and a second region for spectroscopy, for example.

BACKGROUND OF THE INVENTION

MR spectroscopy (MRS) is used for the non-invasive study of cardiac metabolism without the need for the application of external radioactive tracers, such as involved in Positron Emission Tomography (PET). Nuclei of interest for metabolic MRS studies include 1H, 13C, 19F, 23Na, 31P, 39K, 87Rb. Both 31P and 1H-MRS-studies are of clinical interest. Specifically, 1H-MRS is used to measure total creatine and to evaluate the oxygenation of cardiac tissue or to evaluate diet and therapy effects. Also 31P-MRS is used to estimate the energetic state of the heart by analyzing cardiac high-energy phosphate metabolism. In principle, many clinical questions can be addressed with cardiac MRS. However, 31P is the most widely investigated nucleus in cardiac MRS study and is used for determining the T1 relaxation times for Phosphocreatine (PCr) and γ-ATP (adenosine triphosphate), which are used for correcting for the effects of radiofrequency saturation on metabolite ratios such as a PCr/ATP ratio.

Performing clinical cardiac spectroscopy involves a number of problems. Total examination time is relatively long, and motion artifacts including signal contamination by surrounding tissue (chest wall, blood pool) require correction. Motion artifacts from cardiac and respiratory motion have a negative effect on the reliability of myocardial 1H MR spectroscopy. Motion of the heart relative to the volume of interest may lead to reduced spectral resolution and contamination of the 1H MR spectrum by, for example, epicardial fat. In addition, respiratory motion may negatively influence 1H MR spectral resolution by preventing optimal shimming and water suppression. A system according to invention principles addresses these deficiencies and related problems.

SUMMARY OF THE INVENTION

A system for respiratory motion compensated MR imaging or spectroscopy, comprises an MR imaging system. The MR imaging system includes an RF unit comprising an RF coil, transmitter and receiver for adaptively switching, within a single imaging scan, between, transmitting and receiving using a first RF frequency and transmitting and receiving using a second RF frequency different to the first RF frequency. The RF unit transmits and receives using the first RF frequency to acquire a first imaging data set representing a spatially localized first imaging region located on a patient diaphragm. The first imaging data set represents a spatially localized first imaging region used for tracking respiratory movement. The RF unit transmits and receives using the second RF frequency to acquire a second imaging data set representing a spatially localized second imaging region, in response to determining the diaphragm position is within a predetermined window.

DETAILED DESCRIPTION OF THE INVENTION

Respiratory motion compensation using one dimensional/two dimensional (1D/2D) PACE (Prospective Acquisition Correction) based on echoes from designated lines (1D) or areas (2D) termed navigators is known to be used for double-triggered cardiac proton spectroscopy. The double triggering comprises triggering on both a respiratory cycle PACE derived signal and on a cardiac e.g., ECG signal. The navigators measure the displacement of the liver-lung interface during free breathing. The displacement information allows for double triggering on a defined window within the respiratory cycle and on a defined trigger delay after an R-wave based on an ECG signal. Furthermore, the displacement information allows the excitation volume to be shifted by the determined respiratory displacement within the defined window in real-time (volume tracking). Therefore, application of respiratory navigator gating and tracking improves spectral resolution and reproducibility for metabolic imaging of myocardial triglyceride of the human heart.

Figure 1:
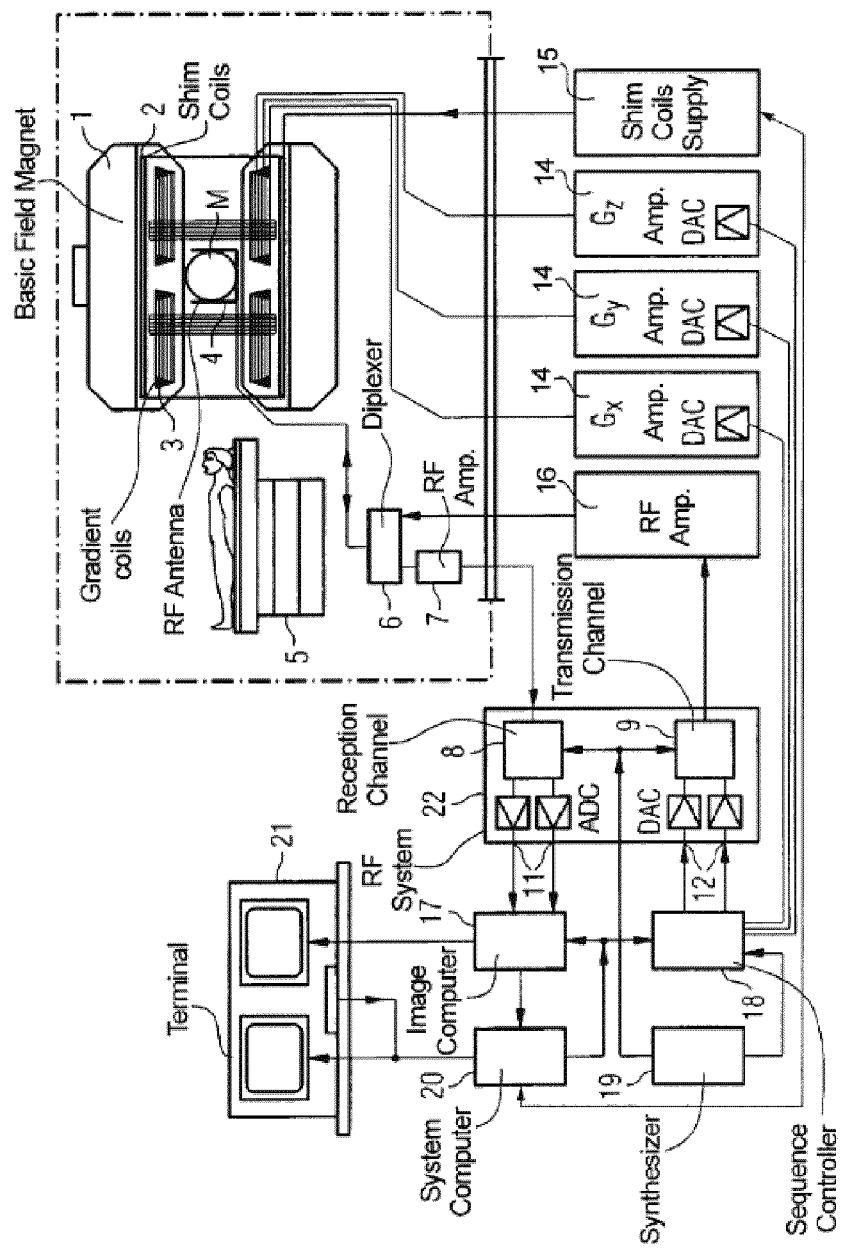
FIG. 1 shows a system for respiratory motion compensated MR imaging or spectroscopy, according to invention principles.

FIG. 1 shows system 10 for respiratory motion compensated MR imaging or spectroscopy. System 10 uses (1D/2D) PACE respiratory motion navigator gating and volume imaging for single (e.g., respiratory motion trigger) or double-triggered (ECG and respiratory motion) Multi Nucleus Cardiac MR Spectroscopy. A basic field magnet 1 generates a strong magnetic field, which is constant in time, for the polarization or alignment of the nuclear spins in the examination region of an object, such as, for example, a part of a human body to be examined. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences are eliminated by shim coils 2, which are controlled by a shim-current supply 15.

In the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times.

Within the gradient field system 3, radio-frequency (RF) coils 4 are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. In one embodiment, RF coils 4 comprise a subset or substantially all of, multiple RF coils arranged in sections along the length of volume M corresponding to the length of a patient. Further, an individual section RF coil of coils 4 comprises multiple RF coils providing RF image data that is used in parallel to generate a single MR image. RF pulse signals are applied to RF coils 4, which in response produce magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via an amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M.

The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17. Imaging computer 17 reconstructs an image from the processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

System computer 20 automatically (or in response to user command entered via terminal 21) employs and directs the MR imaging device of system 10 for MR imaging or spectroscopy. RF coils 4 and RF system 22 transmitters and receivers adaptively switch, within a single imaging scan, between, transmitting and receiving using a first RF frequency and transmitting and receiving using a second RF frequency different to the first RF frequency. RF system 22 transmits and receives using the first RF frequency to acquire a first imaging data set representing a spatially localized first imaging region located on a patient diaphragm used for tracking respiratory movement. RF system 22 transmits and receives using the second RF frequency to acquire a second imaging data set representing a spatially localized second imaging region. The image generator provides spectroscopy data or an MR image for presentation on a reproduction device (e.g., terminal 21).

The MR imaging system of system 10 performs a single imaging scan including, acquiring a first imaging data set representing a spatially localized first imaging region located on a patient diaphragm, using a first RF excitation pulse sequence and transmitting a nuclei excitation first resonant frequency and receiving data substantially at the first resonant frequency. System 10 derives data representing diaphragm position over a respiratory cycle using the first imaging data set. In response to determining the diaphragm position is within a predetermined window and determining a particular point in a patient heart cycle in response to a heart cycle indicative signal (e.g., ECG), system 10 acquires a second anatomical imaging data set representing a spatially localized second imaging region using a second RF excitation pulse sequence and transmits a nuclei excitation second resonant frequency different to the first resonant frequency and receives data substantially at the second resonant frequency. The first imaging region located on the patient diaphragm comprises at least one of, (a) a 1D PACE (one dimensional Prospective Acquisition Correction) compatible line overlapping a patient lung and liver and (b) a 2D PACE (two dimensional Prospective Acquisition Correction) compatible area overlapping a patient lung and liver. The single imaging scan is a single acquisition of a sequence of patient images acquired in response to a user command initiating the scan and system 10 initiates acquisition of the second anatomical imaging data set The first resonant frequency is a 1H (proton) resonant frequency and the second resonant frequency is at least one of, a 31P (phosphorus), 13C (carbon) and 23Na (sodium) isotope resonant frequency. In another embodiment, the first resonant frequency is a 31P (phosphorus) isotope resonant frequency, a 13C (carbon) isotope resonant frequency or a 23Na (sodium) isotope resonant frequency. In a further embodiment, the second resonant frequency in a second imaging scan is a 1H (proton) resonant frequency.

Figure 2:
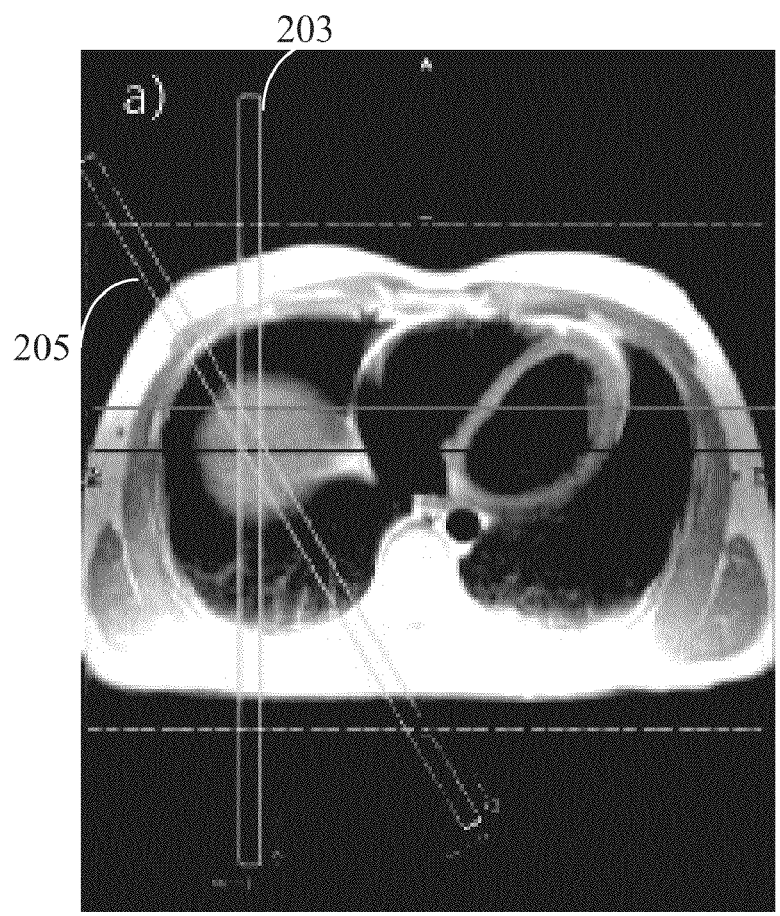
FIG. 2 illustrates positioning of a pencil-shaped volume across a diaphragm for MR imaging detection of respiratory motion using 1D-PACE (one dimensional Prospective Acquisition Correction), according to invention principles.

FIG. 2 illustrates positioning of a pencil-shaped volume across a diaphragm in two positions 203 and 205 corresponding to two points in a respiratory cycle used by system 10 (FIG. 1) for MR imaging detection of respiratory motion using 1D-PACE (one dimensional Prospective Acquisition Correction). The cross-section of the pencil-shaped volume is defined by the intersection of the two pencil-shaped volumes in the axial plane. The length of the pencil-shaped volume is depicted in the coronal plane. The 1D-PACE method of respiratory motion detection is relatively fast and typically performed within 30 ms for minimizing the effects of breathing motion in cardiac imaging examinations. For this purpose, image data representing the pencil-shaped volume comprising a single line of data that crosses the diaphragm is acquired. The volume is interactively placed in such a way that the position of the diaphragm can be calculated and used for motion correction in real time.

Figure 3:
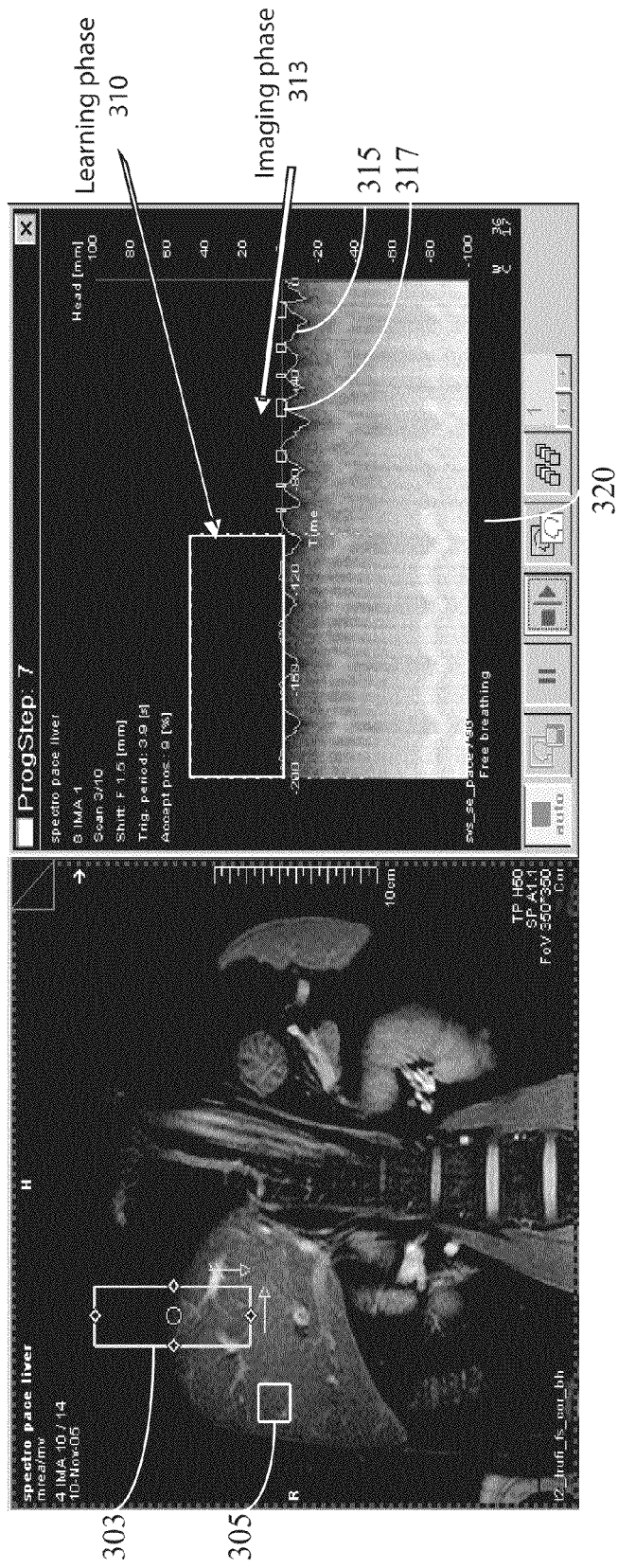
FIG. 3 shows use of a 2D area for detection of a diaphragm position when employing 2D-PACE (two dimensional Prospective Acquisition Correction), according to invention principles.

FIG. 3 shows use of a 2D area for detection of a diaphragm position when employing 2D-PACE (two dimensional Prospective Acquisition Correction). In 2D-PACE, an image is acquired by means of a low-resolution gradient echo sequence featuring a low flip angle, for example. This ensures that magnetization is not saturated, so that dark lines in the image are avoided. A user places a small box 303 across the diaphragm on the 2D image for detection of the diaphragm position. Approximately half the box covers the lungs, the other half the liver. A single voxel spectroscopy (SVS) voxel is represented by box 305. The change in signal intensity along the axis between light and dark portions of box 303 marking the lung-liver boundary is used to determine the position of the diaphragm. Since a 2D image provides more information than a single line, this method is more robust than 1D-PACE. The time used to acquire an image for 2D-PACE is around 100 ms, for example. Image 320 shows a graphical plot of respiratory diaphragm motion 315 indicated by movement of box 303 (y-axis) detected by the system 10 MR imaging device plotted against time (x-axis). The height of the small boxes such as box 317 indicates a predetermined acceptable motion tolerance window for a desired image acquisition. System 10 (FIG. 1) employs 1D/2D PACE respiratory motion detection enabling imaging while a patient is breathing freely to provide a spectroscopy MRI pulse sequence triggered at the quiet end of the expiration phase of a respiratory cycle within a predetermined motion tolerance window 1D/2D PACE. An image acquisition scan includes a learning phase 310 used for determining an acceptable motion tolerance window such as indicated by box 317 and an imaging phase 313 used for acquiring MR spectroscopy data within a determined acceptable motion tolerance window.

Figure 4:
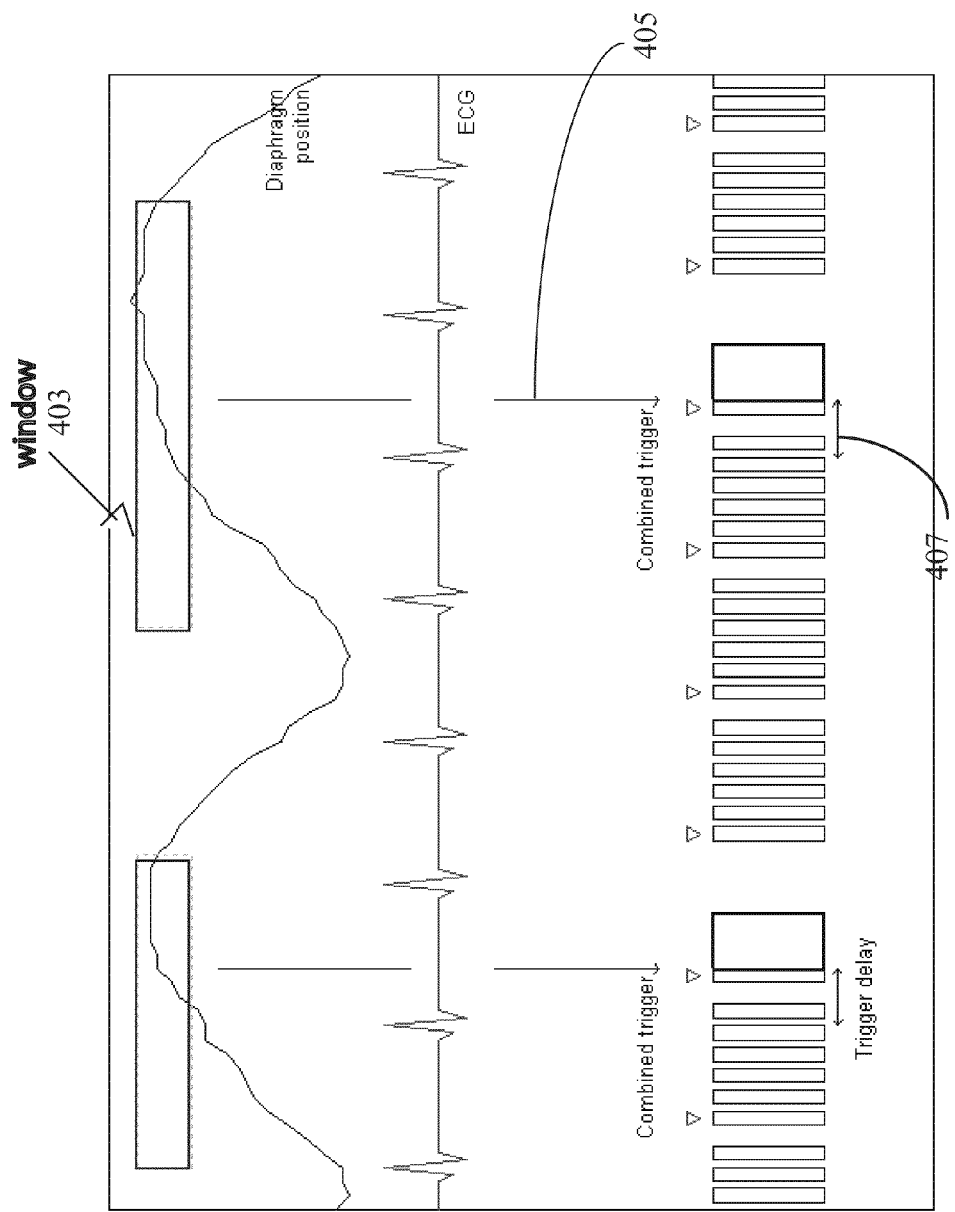
FIG. 4 shows detection of a diaphragm position within a window as a first trigger in conjunction with heart cycle second trigger for image acquisition, according to invention principles.

FIG. 4 shows detection of a diaphragm position within a predetermined window 403 as a first trigger in conjunction with a heart cycle (ECG) second trigger 405 for image acquisition. A navigator identified within predetermined window 405 enables creation of a trigger event. After an R-wave has been detected a temporal position of a navigator window is adjusted in real time such that it encompasses a trigger comprising a predetermined delay time 407 following an R-wave. If the diaphragm position measured by the flagged navigator falls into the acceptance window it triggers the anatomical imaging sequence. Otherwise navigator polling is continued.

Figure 5:
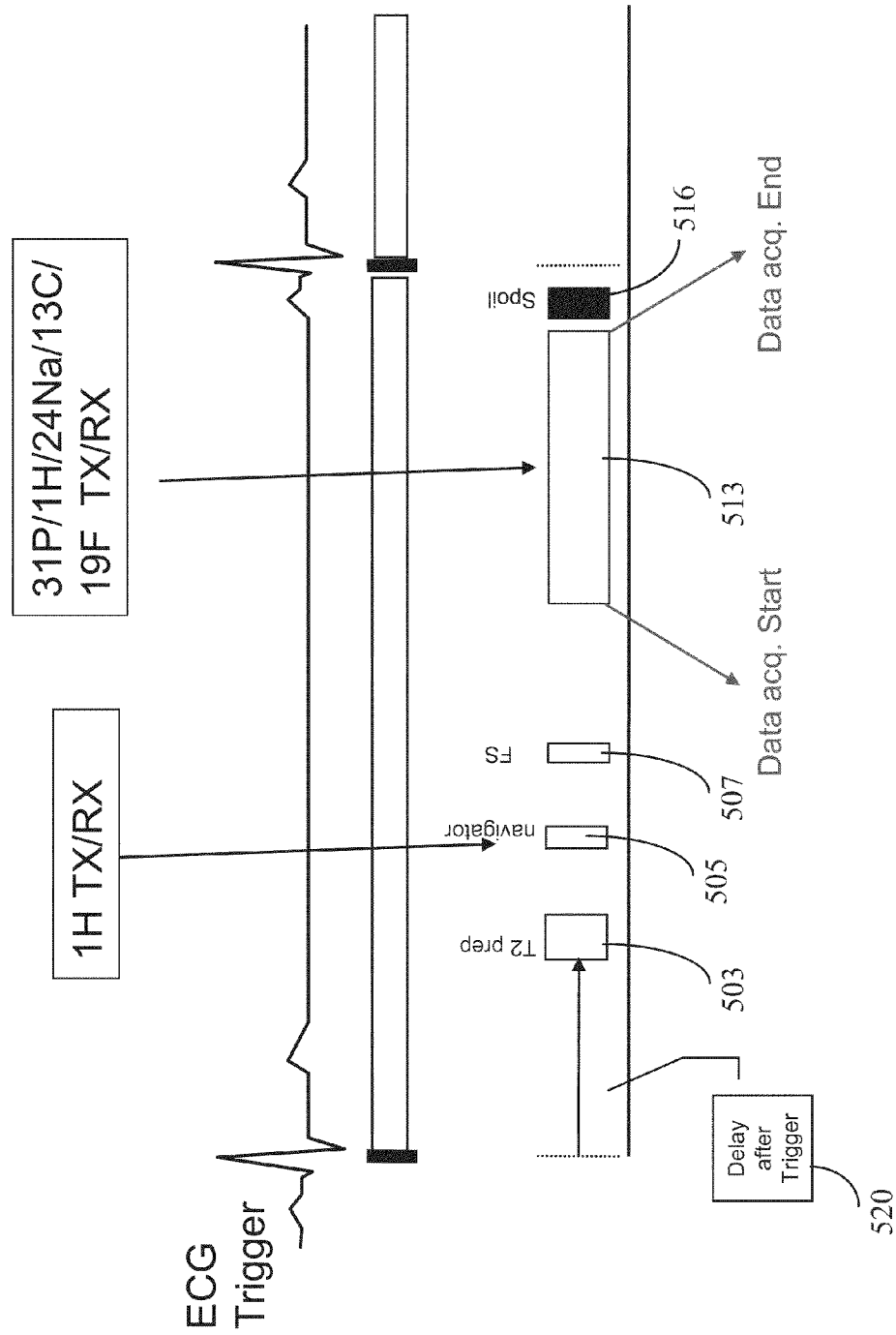
FIG. 5 illustrates 1D PACE and multi nucleus MRI/MRS using first and second RF frequencies to acquire first and second imaging data sets for tracking respiratory movement and imaging a spatially localized second imaging region, respectively, according to invention principles.

FIG. 5 illustrates 1D PACE and multi nucleus MRI/MRS using first and second RF frequencies to acquire first and second imaging data sets for tracking respiratory movement and imaging a spatially localized second imaging region, respectively. Specifically system 10 (FIG. 1) employs a T2-weighted transversal fat saturation spin echo pulse sequence. The pulse sequence provides T2-weighted magnetization preparation 503 following an ECG R-wave by delay 520 as well as RF transmission and receiving of a first resonant frequency for imaging acquisition 505 of a spatially localized 1D diaphragm region. The pulse sequence further involves a fat saturation magnetization 507 and RF transmission and receiving of a second RF resonant frequency for image acquisition in window 513 for acquiring a second imaging data set representing a spatially localized second imaging region e.g., of one or more voxels for spectroscopy. The MR imaging system initiates acquisition of the second anatomical imaging data set substantially at a particular point in a patient heart cycle in response to a heart cycle indicative signal. A spoiler magnetizing gradient 516 is applied to reset k-space and coil magnetization to a substantially null position. The first resonant frequency is a 1H (proton) resonant frequency and the second resonant frequency is at least one of a 13C (carbon), 24Na, 13C or 19F isotope resonant frequency. The second resonant frequency in a second imaging scan is a 1H (proton) resonant frequency and the first resonant frequency is at least one of, a 13C (carbon), 1H, 24Na, 13C or 19F isotope resonant frequency. In contrast, because of the low content of non 1H proton from the liver region, respiratory motion gated and ECG-triggered MR spectroscopy of the human heart in known systems is typically focused on 1H MR spectroscopy study.

Figure 6:
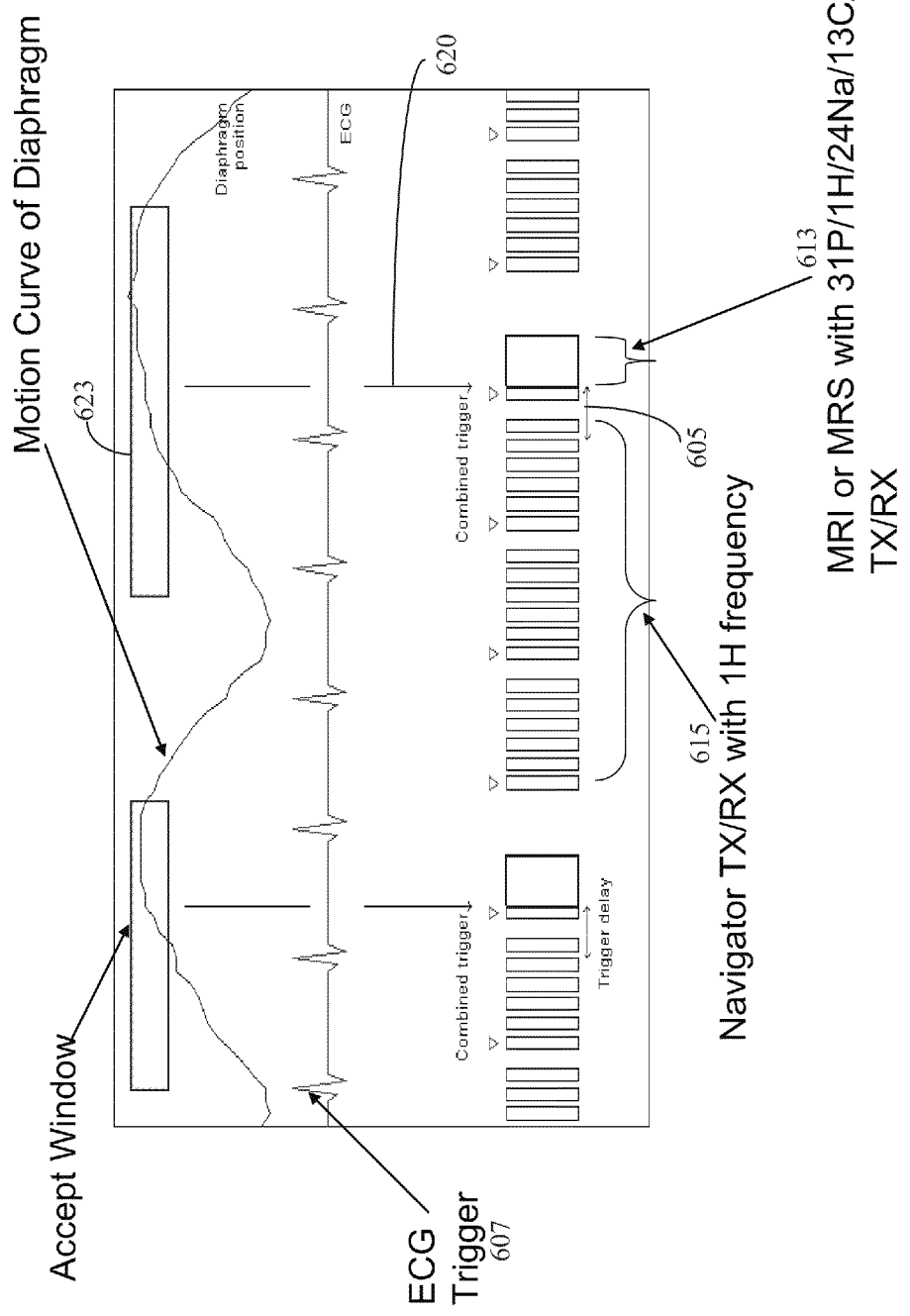
FIG. 6 illustrates 2D PACE and multi nucleus MRI/MRS using first and second RF frequencies to acquire first and second imaging data sets for tracking respiratory movement and imaging a spatially localized second imaging region, respectively, according to invention principles.

FIG. 6 illustrates 2D PACE and multi nucleus MRI/MRS using first and second RF frequencies employed by system 10 (FIG. 1) to acquire first and second imaging data sets for tracking respiratory movement and imaging a spatially localized second imaging region, respectively. Specifically, system 10 (including RF unit 22) performs a single imaging scan using 2D PACE by acquiring first imaging data set 615 representing a spatially localized first imaging region located on a patient diaphragm used for tracking respiratory movement. System 10 uses a first RF excitation pulse sequence and transmits a nuclei excitation first resonant frequency and receives data substantially at the first resonant frequency. RF unit 22 and RF coils 4 comprise a transmitter and receiver for adaptively switching, within a single imaging scan, between, transmitting and receiving using a first RF frequency and transmitting and receiving using a second RF frequency different to the first RF frequency. RF unit 22 transmits and receives using the second RF frequency to acquire second imaging data set 613 representing a spatially localized second imaging region. MR imaging system 10 initiates RF unit 22 in transmitting and receiving using the second RF frequency in response to a determination of diaphragm location derived using the first imaging data set. An image data processor in imaging computer 17 processes image data of the second imaging data set to compensate for respiratory displacement in response to a determination of diaphragm location derived using the first imaging data set.

System 10 derives data representing diaphragm position over a respiratory cycle using the first imaging data set and applies a threshold to determine when the diaphragm position is within window 623. In response to a combined trigger 620 determined at a point occurring a predetermined delay 605 following an ECG signal 607 R-wave pulse in conjunction with a diaphragm position being within predetermined window 623, system 10 acquires second anatomical imaging data set 613 using a second RF excitation pulse sequence and transmitting a nuclei excitation second resonant frequency different to the first resonant frequency and receiving data substantially at the second resonant frequency. The first resonant frequency is a 1H (proton) resonant frequency and the second resonant frequency is at least one of a 13C (carbon), 24Na, 13C or 19F isotope resonant frequency. The second resonant frequency in a second imaging scan is a 1H (proton) resonant frequency and the first resonant frequency is at least one of, a 13C (carbon), 24Na, 13C or 19F isotope resonant frequency.

Figure 7:
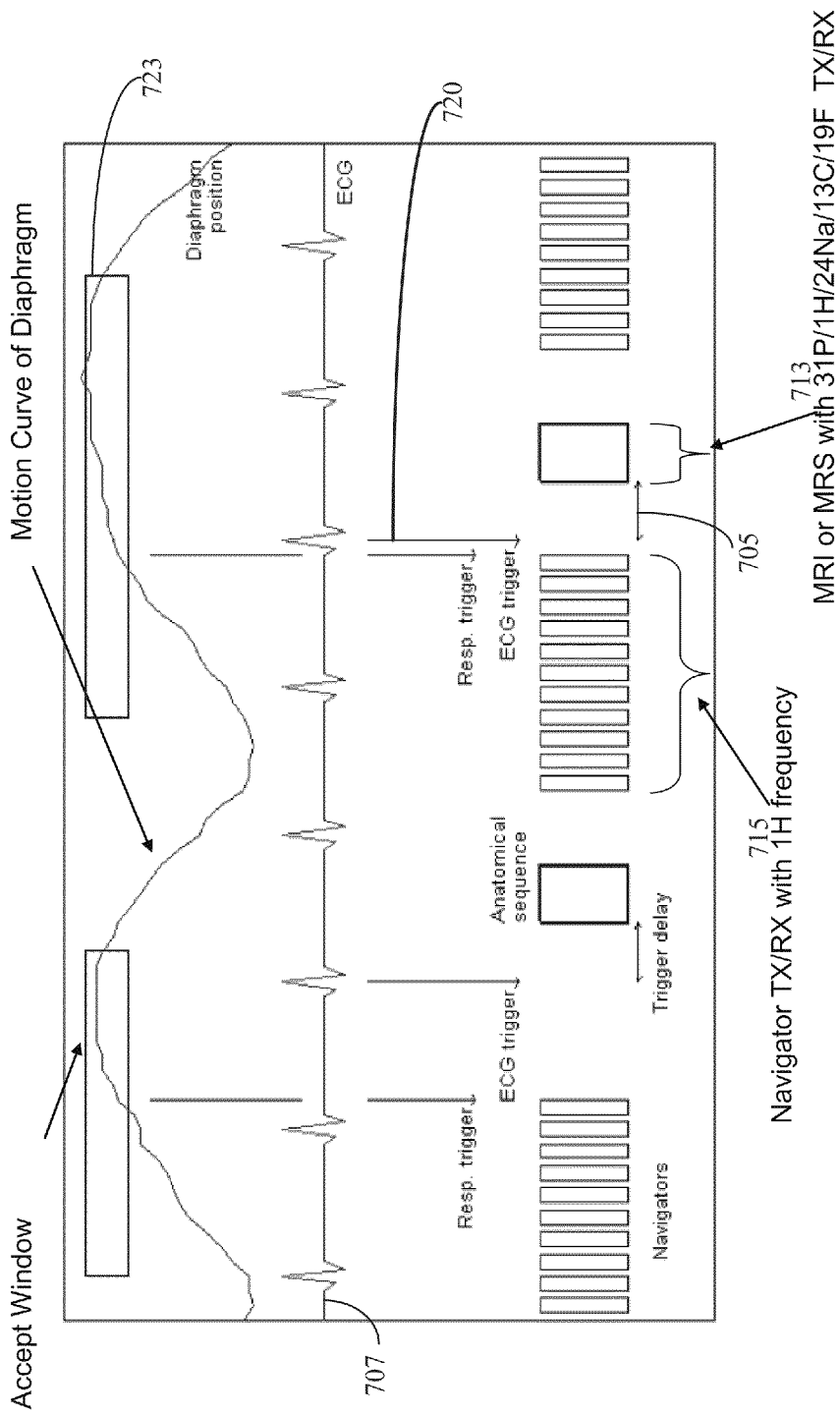
FIG. 7 illustrates a further 2D PACE multi nucleus MRI/MRS trigger arrangement using first and second RF frequencies to acquire first and second imaging data sets for tracking respiratory movement and imaging a spatially localized second imaging region, respectively, according to invention principles.

FIG. 7 illustrates a further 2D PACE multi nucleus MRI/MRS trigger arrangement using first and second RF frequencies employed by system 10 (FIG. 1) to acquire first and second imaging data sets for tracking respiratory movement and imaging a spatially localized second imaging region, respectively. Similar to FIG. 6, system 10 (FIG. 1) performs a single imaging scan using 2D PACE by acquiring a first imaging data set 715 representing a spatially localized first imaging region located on a patient diaphragm, using a first RF excitation pulse sequence and transmitting a nuclei excitation first resonant frequency and receiving data substantially at the first resonant frequency. System 10 derives data representing diaphragm position over a respiratory cycle using the first imaging data set and applies a threshold to determine when the diaphragm position is within window 723. In response to a trigger 720 determined at a point occurring a predetermined delay 705 following an ECG signal 707 R-wave pulse and a diaphragm position being detected within predetermined window 723, system 10 acquires a second anatomical imaging data set 713 representing a spatially localized second imaging region using a second RF excitation pulse sequence and transmitting a nuclei excitation second resonant frequency different to the first resonant frequency and receiving data substantially at the second resonant frequency. The spatially localized second imaging region comprises a voxel, pixel or group of pixels, for example.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system provides respiratory motion compensated spectroscopy or imaging by double triggering on both a respiratory cycle (1D/2D) PACE derived signal and on a cardiac e.g., ECG signal and to shift an RF excitation volume (volume tracking) to improve spectral resolution and reproducibility of metabolic imaging. Further, the processes and applications may, in alternative embodiments, be located on one or more (e.g., distributed) processing devices on a network linking the units of FIG. 1. Any of the functions and steps provided in FIGS. 1-7 may be implemented in hardware, software or a combination of both.

What is claimed is:

1. A system for respiratory motion compensated MR imaging or spectroscopy, comprising:
an MR imaging system for performing a single imaging scan including,
(a) acquiring a first imaging data set representing a spatially localized first imaging region located on a patient diaphragm, using a first RF excitation pulse sequence and transmitting a nuclei excitation first resonant frequency and receiving data substantially at said first resonant frequency,
(b) deriving data representing diaphragm position over a respiratory cycle using said first imaging data set, and
(c) in response to determining said diaphragm position is within a predetermined window, acquiring a second anatomical imaging data set representing a spatially localized second imaging region using a second RF excitation pulse sequence and transmitting a nuclei excitation second resonant frequency different to said first resonant frequency and receiving data substantially at said second resonant frequency.

2. A system according to claim 1, wherein
said single imaging scan is a single acquisition of a sequence of patient images acquired in response to a user command initiating the scan.

3. A system according to claim 1, wherein
said first imaging region located on said patient diaphragm comprises at least one of, (a) a 1D PACE (one dimensional Prospective Acquisition Correction) compatible line overlapping a patient lung and liver and (b) a 2D PACE (two dimensional Prospective Acquisition Correction) compatible area overlapping a patient lung and liver.

4. A system according to claim 1, wherein
said MR imaging system initiates acquisition of said second anatomical imaging data set substantially at a particular point in a patient heart cycle in response to a heart cycle indicative signal.

5. A system according to claim 1, wherein
said first resonant frequency is a 1H (proton) resonant frequency and said second resonant frequency is a 31P (phosphorus) isotope resonant frequency.

6. A system according to claim 1, wherein
said first resonant frequency is a 1H (proton) resonant frequency and said second resonant frequency is a 13C (carbon) isotope resonant frequency or a 23Na (sodium) isotope resonant frequency.

7. A system according to claim 6, wherein
said second resonant frequency in a second imaging scan is a 1H (proton) resonant frequency.

8. A system according to claim 1, wherein
said first resonant frequency is a at least one of, (a) a 31P (phosphorus) isotope resonant frequency, (b) a 13C (carbon) isotope resonant frequency and (c) a 23Na (sodium) isotope resonant frequency.

9. A method for respiratory motion compensated MR imaging or spectroscopy using an MR imaging system, comprising the activities of:
performing a single imaging scan including,
(a) acquiring a first imaging data set representing a spatially localized first imaging region located on a patient diaphragm, using a first RF excitation pulse sequence and transmitting a nuclei excitation first resonant frequency and receiving data substantially at said first resonant frequency,
(b) deriving data representing diaphragm position over a respiratory cycle using said first imaging data set, and
(c) in response to determining said diaphragm position is within a predetermined window and in response to determining a particular point in a patient heart cycle using a heart cycle indicative signal, acquiring a second anatomical imaging data set representing a spatially localized second imaging region using a second RF excitation pulse sequence and transmitting a nuclei excitation second resonant frequency different to said first resonant frequency and receiving data substantially at said second resonant frequency.

10. A method according to claim 9, wherein
said spatially localized second imaging region comprises at least one of, (a) a voxel, (b) a pixel and (c) a group of pixels.

11. A system for respiratory motion compensated MR imaging or spectroscopy, comprising:
an MR imaging system including,
an RF unit comprising an RF coil, transmitter and receiver for adaptively switching, within a single imaging scan, between, transmitting and receiving using a first RF frequency and transmitting and receiving using a second RF frequency different to said first RF frequency,
said RF unit transmitting and receiving using said first RF frequency to acquire a first imaging data set representing a spatially localized first imaging region located on a patient diaphragm, said first imaging data set representing a spatially localized first imaging region used for tracking respiratory movement and
said RF unit transmitting and receiving using said second RF frequency to acquire a second imaging data set representing a spatially localized second imaging region.

12. A system according to claim 11, wherein
said MR imaging system initiates said RF unit in transmitting and receiving using said second RF frequency in response to a determination of diaphragm location derived using said first imaging data set.

13. A system according to claim 11, including
an image data processor for processing image data of said second imaging data set to compensate for respiratory displacement in response to a determination of diaphragm location derived using said first imaging data set.

* * * * *